(12) United States Patent
Carter et al.

(10) Patent No.: US 12,161,873 B2
(45) Date of Patent: Dec. 10, 2024

(54) HEADER CONNECTION SYSTEM FOR IMPLANTABLE MEDICAL DEVICE

(71) Applicant: Greatbatch Ltd., Clarence, NY (US)

(72) Inventors: Scott Carter, Orchard Park, NY (US); Luis Daniel Villamil, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 612 days.

(21) Appl. No.: 17/384,193

(22) Filed: Jul. 23, 2021

(65) Prior Publication Data

US 2022/0023643 A1 Jan. 27, 2022

Related U.S. Application Data

(60) Provisional application No. 63/056,242, filed on Jul. 24, 2020.

(51) Int. Cl.
*A61N 1/375* (2006.01)

(52) U.S. Cl.
CPC .................... *A61N 1/3752* (2013.01)

(58) Field of Classification Search
None
See application file for complete search history.

(56) References Cited

U.S. PATENT DOCUMENTS

| | | |
|---|---|---|
| 6,862,478 B1 | 3/2005 | Goldstein |
| 6,878,013 B1 | 4/2005 | Behan et al. |
| 7,083,474 B1 | 8/2006 | Fleck et al. |
| 7,110,827 B2 | 9/2006 | Sage et al. |
| 7,167,749 B2 | 1/2007 | Biggs et al. |
| 7,402,076 B1 | 7/2008 | Lim et al. |
| 7,751,893 B2 | 7/2010 | Biggs et al. |
| 7,798,862 B2 | 9/2010 | Kast et al. |
| 8,091,226 B2 | 1/2012 | Sjostedt et al. |
| 8,527,054 B2 | 9/2013 | North |
| 9,088,093 B2 | 7/2015 | Reisinger et al. |
| 9,345,894 B2 | 5/2016 | Sweeney et al. |
| 9,555,256 B2 | 1/2017 | Jullien et al. |
| 9,687,661 B2 | 6/2017 | Bortolin et al. |
| D792,593 S | 7/2017 | Lim |
| 10,232,186 B2 | 3/2019 | Sweeney et al. |
| 10,256,590 B2 | 4/2019 | Spadgenske |

(Continued)

FOREIGN PATENT DOCUMENTS

WO 2016172245 A1 10/2016

*Primary Examiner* — William J Levicky
*Assistant Examiner* — Daniel Tehrani
(74) *Attorney, Agent, or Firm* — Michael P. Horvath

(57) ABSTRACT

In various examples, a header of an implantable device includes a first header portion and a second header portion at least partially disengageable from the first header portion. In a closed configuration, the first header portion is fully engaged with the second header portion, and in an open configuration, the first header portion is at least partially disengaged from the second header portion. At least one bore within the header is sized and shaped to accommodate a proximal end of a lead. The bore is split substantially longitudinally to form a first bore portion and a second bore portion. With the proximal end of the lead disposed within the bore and a positioning feature interacting with a lead feature, at least one lead contact aligns with at least one header contact to allow the at least one lead contact to electrically couple to the at least one header contact.

20 Claims, 9 Drawing Sheets

(56) References Cited

U.S. PATENT DOCUMENTS

| | | | |
|---|---|---|---|
| 2008/0255631 A1* | 10/2008 | Sjostedt | A61N 1/3752 |
| | | | 607/37 |
| 2012/0130438 A1* | 5/2012 | Seeley | H01R 24/76 |
| | | | 607/2 |
| 2013/0035730 A1 | 2/2013 | Erickson et al. | |
| 2013/0150916 A1 | 6/2013 | Kane et al. | |
| 2019/0374776 A1 | 12/2019 | Mishra et al. | |
| 2020/0254263 A1* | 8/2020 | Deininger | A61N 1/375 |

* cited by examiner

HEADER CONNECTION SYSTEM FOR IMPLANTABLE MEDICAL DEVICE

CROSS REFERENCE TO RELATED APPLICATIONS

This application claims the benefit of priority to U.S. Provisional Application Ser. No. 63/056,242, filed on Jul. 24, 2020, entitled "HIGH DENSITY HEADER CONNECTION SYSTEM," which is incorporated by reference herein in its entirety.

BACKGROUND

Implantable medical devices are commonly implanted within patients for various reasons, including, for instance, electrical tissue stimulation, physiological parameter measuring and/or monitoring, and/or drug dispensing. Such implantable medical devices often include one or more leads or other components coupled to a header, the header acting to electrically connect the one or more leads or other components to electronics disposed within the implantable medical device. Oftentimes, such a lead or other component is inserted within a bore hole disposed within a header of the implantable medical device. This is often accomplished by applying force longitudinally (axially) along the lead to push a proximal end of the lead into the bore and, in turn, into contact with one or more contacts disposed within the bore. As the need increases for implantable medical devices with more and more electrodes, contacts, or channels and/or the desire increases to reduce the size of implantable medical devices and the leads and components associated with the implantable medical devices, insertion of leads or other components into bores in this way becomes more and more difficult. Insertion force needed to insert leads and other components into bores increases as the number of contacts through which the proximal end of the lead or other component increases. Moreover, axial stiffness of a lead or other component typically decreases as the size of such a lead or other component decreases, resulting in decreased pushability of the lead or other component into a bore.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to provide an implantable medical device that is smaller in size and higher in channel count than a conventional implantable medical device. In various examples, the present subject matter is advantageous in that it provides for very low insertion force to be applied to the lead during insertion of the lead into a header or other component of an implantable medical device, thereby inhibiting or lessening damage to the lead (mechanically or electrically) during an implant procedure and connection of the lead to the implantable medical device. In some examples, the present invention allows for connection and fixation of more than one multi-contact lead in a single operation. In some examples, the present invention can employ a positioning feature to facilitate alignment of the lead and the header contacts. In some examples, the present invention can employ a lead securing feature to inhibit the lead from moving without the need for a set screw, thereby eliminating the possibility of a set screw pressing on and potentially damaging the lead. To better illustrate the devices and methods described herein, a non-limiting list of examples is provided here:

Example 1 can include subject matter that can include a header of an implantable device. The implantable device includes a housing and a lead. The housing includes electronics disposed within the housing. The lead includes an elongate body with a proximal end and a distal end. The lead includes at least one lead contact proximate the proximal end and at least one lead electrode proximate the distal end. The header includes a first header portion and a second header portion at least partially disengageable from the first header portion. The header includes a closed configuration in which the first header portion is fully engaged with the second header portion and an open configuration in which the first header portion is at least partially disengaged from the second header portion. At least one bore within the header is sized and shaped to accommodate the proximal end of the lead. The bore includes a bore opening in a wall of the header. The bore is split substantially longitudinally to form a first bore portion and a second bore portion. The first bore portion forms a first channel disposed within the first header portion and includes a first channel opening in a first surface of the first header portion along a length of the first channel. The second bore portion forms a second channel disposed within the second header portion and includes a second channel opening in a second surface of the second header portion along a length of the second channel. At least one header contact is disposed within the bore and configured to electrically couple to the lead contact with the proximal end of the lead disposed within the bore. A positioning feature is disposed within the bore. The positioning feature is configured to interact with a corresponding lead feature proximate the proximal end of the lead. With the proximal end of the lead disposed within the bore and the positioning feature interacting with the lead feature, the at least one lead contact aligns with the at least one header contact to allow the at least one lead contact to electrically couple to the at least one header contact. With the header in the open configuration, the length of the first bore portion is accessible to allow the lead to be inserted within the first channel through the first channel opening. With the header in the closed configuration, the first surface of the first header portion abuts the second surface of the second header portion so that the first bore portion and the second bore portion form the bore accessible only through the bore opening in the wall of the header, such that, with the proximal end of the lead disposed within the bore, the elongate body of the lead extends distally from the bore opening.

In Example 2, the subject matter of Example 1 is optionally configured such that the positioning feature includes a pin disposed within the bore and the lead feature includes a corresponding hole within the lead proximate the proximal end of the lead. The hole is complementary to the pin, such that, with the proximal end of the lead disposed within the bore and the pin disposed within the hole of the lead, the lead is positioned within the bore to allow the at least one lead contact to align with and electrically couple to the at least one header contact.

In Example 3, the subject matter of Example 1 or 2 is optionally configured such that the positioning feature includes a protrusion disposed within the bore and the lead feature includes a corresponding indentation within the lead proximate the proximal end of the lead. The indentation is complementary to the protrusion, such that, with the proximal end of the lead disposed within the bore and the protrusion disposed within the indentation of the lead, the lead is positioned within the bore to allow the at least one lead contact to align with and electrically couple to the at least one header contact.

In Example 4, the subject matter of Example 3 is optionally configured such that the protrusion includes a bump extending into the bore and the indentation includes a notch within the lead.

In Example 5, the subject matter of Example 3 is optionally configured such that the protrusion includes one or more radially-extending bumps extending into and disposed at least partially around the bore and the indentation includes a groove disposed within and extending at least partially radially around the lead.

In Example 6, the subject matter of any one of Examples 1-5 is optionally configured such that the at least one header contact includes a spring.

In Example 7, the subject matter of any one of Examples 1-6 is optionally configured such that the at least one header contact includes a spring contact.

In Example 8, the subject matter of any one of Examples 1-7 optionally includes a seal member including a first seal portion disposed within the first bore portion of the first header portion and a second seal portion disposed within the second bore portion of the second header portion. With the header in the closed configuration and the proximal end of the lead within the bore, the first seal portion abuts the second seal portion and the first seal portion and the second seal portion extends into the bore to abut the elongate body of the lead.

In Example 9, the subject matter of any one of Examples 1-8 is optionally configured such that the first header portion is pivotably coupled to the second header portion, such that the second header portion is rotatable with respect to the first header portion from being fully engaged with the first header portion in the closed configuration to being partially disengaged from the first header portion in the open configuration.

In Example 10, the subject matter of Example 9 is optionally configured such that the first header portion is pivotably coupled to the second header portion at a hinge.

In Example 11, the subject matter of any one of Examples 1-10 is optionally configured such that the first header portion is removably coupled to the second header portion, such that the second header portion is fully engaged with the first header portion in the closed configuration and fully disengaged and removed from the first header portion in the open configuration.

In Example 12, the subject matter of Example 11 is optionally configured such that the first header portion is removably coupled to the second header portion using securement members.

Example 13 can include, or can optionally be combined with any one of Examples 1-12 to include subject matter that can include an implantable device a housing including electronics disposed within the housing. A lead includes an elongate body with a proximal end and a distal end. The lead includes at least one lead contact proximate the proximal end and at least one lead electrode proximate the distal end. A header is attached to the housing. The header is configured to engage with the lead and electrically couple the lead to the electronics disposed within the housing. The header includes a first header portion and a second header portion at least partially disengageable from the first header portion. The header includes a closed configuration in which the first header portion is fully engaged with the second header portion and an open configuration in which the first header portion is at least partially disengaged from the second header portion. At least one bore within the header is sized and shaped to accommodate the proximal end of the lead. The bore includes a bore opening in a wall of the header. The bore is split substantially longitudinally to form a first bore portion and a second bore portion. The first bore portion forms a first channel disposed within the first header portion and includes a first channel opening in a first surface along a length of the first channel. The second bore portion forms a second channel disposed within the second header portion and includes a second channel opening in a second surface along a length of the second channel. At least one header contact is disposed within the bore and configured to electrically couple to the lead contact with the proximal end of the lead disposed within the bore. A positioning feature is disposed within the bore. The positioning feature is configured to interact with a corresponding lead feature proximate the proximal end of the lead, wherein, with the proximal end of the lead disposed within the bore and the positioning feature interacting with the lead feature, the at least one lead contact aligns with the at least one header contact to allow the at least one lead contact to electrically couple to the at least one header contact. With the header in the open configuration, the length of the first bore portion is accessible to allow the lead to be inserted within the first channel through the first channel opening. With the header in the closed configuration, the first surface of the first header portion abuts the second surface of the second header portion so that the first bore portion and the second bore portion form the bore accessible only through the bore opening in the wall of the header, such that, with the proximal end of the lead disposed within the bore, the elongate body of the lead extends distally from the bore opening.

In Example 14, the subject matter of Example 13 is optionally configured such that the positioning feature includes a pin disposed within the bore and the lead feature includes a corresponding hole within the lead proximate the proximal end of the lead. The hole is complementary to the pin, such that, with the proximal end of the lead disposed within the bore and the pin disposed within the hole of the lead, the lead is positioned within the bore to allow the at least one lead contact to align with and electrically couple to the at least one header contact.

In Example 15, the subject matter of Example 13 or 14 is optionally configured such that the positioning feature includes a protrusion disposed within the bore and the lead feature includes a corresponding indentation within the lead proximate the proximal end of the lead. The indentation is complementary to the protrusion, such that, with the proximal end of the lead disposed within the bore and the protrusion disposed within the indentation of the lead, the lead is positioned within the bore to allow the at least one lead contact to align with and electrically couple to the at least one header contact.

In Example 16, the subject matter of Example 15 is optionally configured such that the protrusion includes a bump extending into the bore and the indentation includes a notch within the lead.

In Example 17, the subject matter of any one of Examples 13-16 is optionally configured such that the header includes a seal member including a first seal portion disposed within the first bore portion of the first header portion and a second seal portion disposed within the second bore portion of the second header portion. With the header in the closed configuration and the proximal end of the lead within the bore, the first seal portion abuts the second seal portion and the first seal portion and the second seal portion extends into the bore to abut the elongate body of the lead.

In Example 18, the subject matter of any one of Examples 13-17 is optionally configured such that the first header portion is pivotably coupled to the second header portion, such that the second header portion is rotatable with respect to the first header portion from being fully engaged with the first header portion in the closed configuration to being partially disengaged from the first header portion in the open configuration.

In Example 19, the subject matter of any one of Examples 13-18 is optionally configured such that the first header portion is removably coupled to the second header portion, such that the second header portion is fully engaged with the first header portion in the closed configuration and fully disengaged and removed from the first header portion in the open configuration.

Example 20 can include, or can optionally be combined with any one of Examples 1-19 to include subject matter that can include a header of an implantable device. The header includes a first header portion and a second header portion at least partially disengageable from the first header portion. The header includes a closed configuration in which the first header portion is fully engaged with the second header portion and an open configuration in which the first header portion is at least partially disengaged from the second header portion. At least one bore within the header is sized and shaped to accommodate a proximal end of a lead. The bore includes a bore opening in a wall of the header. The bore is split substantially longitudinally to form a first bore portion and a second bore portion. The first bore portion forms a first channel disposed within the first header portion and includes a first channel opening in a first surface of the first header portion along a length of the first channel. The second bore portion forms a second channel disposed within the second header portion and includes a second channel opening in a second surface of the second header portion along a length of the second channel. At least one header contact is disposed within the bore and configured to electrically couple to a lead contact with the proximal end of the lead disposed within the bore. A positioning feature is disposed within the bore. The positioning feature is configured to interact with a corresponding lead feature proximate the proximal end of the lead. With the header in the open configuration, the length of the first bore portion is accessible to allow a lead to be inserted within the first channel through the first channel opening. With the header in the closed configuration, the first surface of the first header portion abuts the second surface of the second header portion so that the first bore portion and the second bore portion form the bore accessible only through the bore opening in the wall of the header.

DETAILED DESCRIPTION

Figure 1:
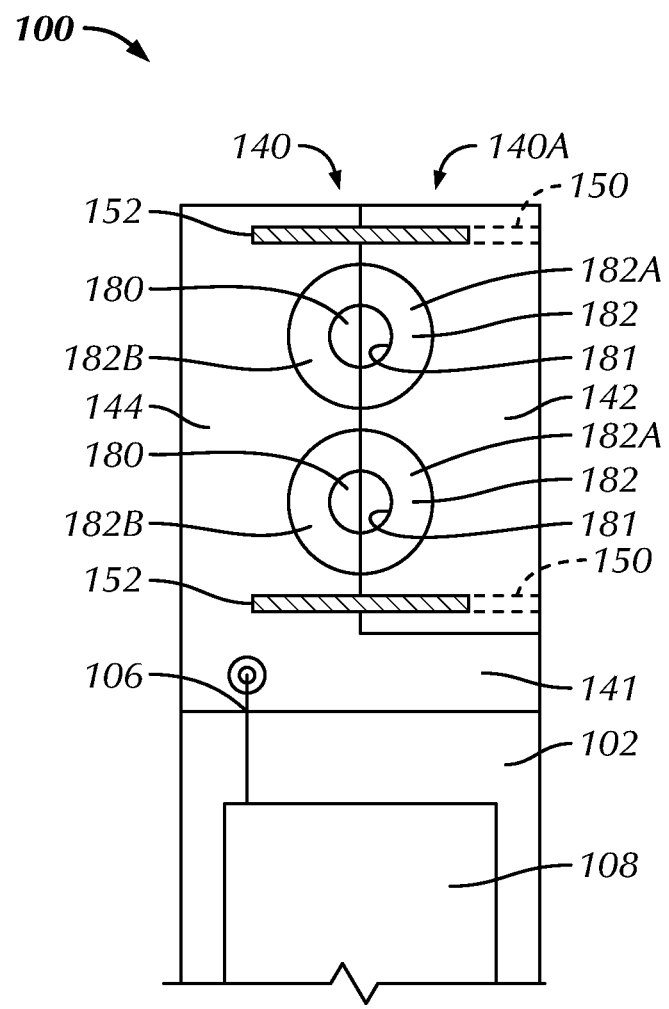
FIG. 1 is a side view of an implantable medical device header in accordance with at least one example of the invention.

The present invention relates generally to providing an implantable medical device that is smaller in size and higher in channel count than a conventional implantable medical device. More specifically, the relatively small, relatively high-channel-count implantable medical devices of the present subject matter allow for very low insertion force applied to the lead during insertion of the lead into a header or other component of an implantable medical device, thereby inhibiting or lessening damage to the lead during an implant procedure and connection of the lead to the implantable medical device.

In some examples, an implantable device header system allows for a higher density of electrical contacts between a stimulation/sensing lead and a device header. With such a configuration, the present inventive subject matter can reduce a size of the implantable device. This reduced size, in some examples, allows the implantable device to be implanted in smaller areas, such as, for instance, the cranium or peripherals, with minimal impact to the body. In some examples, a reduced size of the implantable device can also provide more comfort to the patient when implanted in any area of the body.

In some examples, the present inventive subject matter can lessen or inhibit damage to the lead by reducing the force necessary to apply to the lead in order to insert it within the device header. Conventional implantable device systems require a lead to be inserted into a cylindrical hole or bore in the header, sliding past the electrical contacts and sealing membranes and then secured in place with a set screw. Pushing the lead through the sealing membranes used for electrical insulation and to the electrical contacts creates friction and forces on the lead. High channel count leads increase the number of membranes and therefore increase the insertion force required to insert the lead into the bore to the point that the lead can be damaged during connection.

Conventional implantable device systems can be large and bulky for large channel count leads and/or headers of large channel counts, such as, for instance, more than eight contacts. Often, high-density connectors of such conventional large-channel-count implantable device systems are oddly shaped (that is, not cylindrical) and cannot pass through a conventional catheter. In some examples, the present inventive subject matter allows for the lead to be substantially cylindrical and pass through a conventional catheter or tube prior to connecting with the implantable device. In some examples, the present inventive subject matter allows for high channel count leads with a single connector sequence of contacts. In some examples, the present inventive subject matter allows for connecting and fixing of more than one multi-contact lead in a single operation. In some examples, this present inventive subject matter includes a positioning feature to align the lead and header contacts. The present inventive subject matter, in some examples, includes a lead securing feature that inhibits the lead from moving without requiring a set screw, which would press on the lead. In some examples, the present inventive subject matter includes a clam shell, self-aligned feature to mitigate risk during implant procedure. In further examples, the present inventive subject matter uses a clam shell, self-aligned connection design where the one or more leads are placed in the header and positioned with a positioning feature and then the header is closed and secured over the one or more leads. In some examples, the positioning feature is used to align the electrical contacts between the one or more leads and the header. Issues can arise in current header designs if the lead is not inserted fully into the header and the electrical contacts between the lead and header are misaligned. In some examples, the connector system of the present inventive subject matter maintains electrical insulation of individual contacts as required by implantable devices in the presence of body fluids.

In some examples, the one or more stimulation and/or sensing leads used can be cylindrical with full round or partial lead contacts to provide electrical contact to the header. In some examples, the lead contacts are spaced to match the header contacts within the header with spaces between the lead contacts for contact with the sealing members for electrical insulation.

Figure 2:
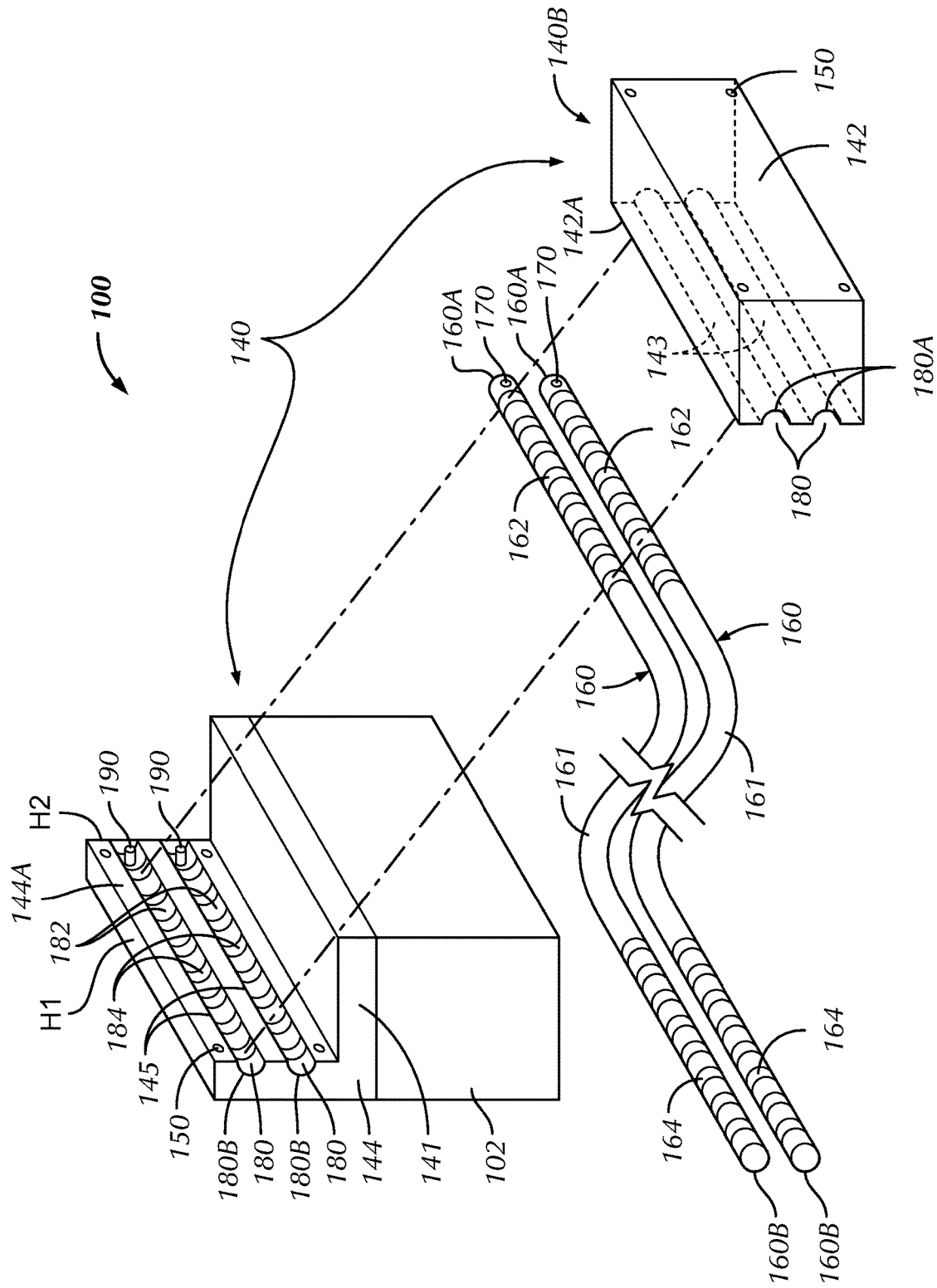
FIG. 2 is an exploded perspective view of an implantable medical device including a header in accordance with at least one example of the invention.
Figure 3A:
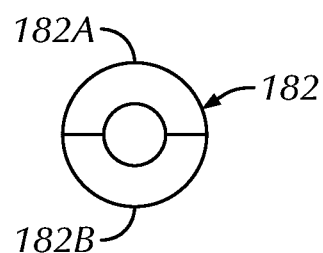
FIGS. 3A and 3B are side views of seals of an implantable medical device header in accordance with at least one example of the invention.
Figure 3B:
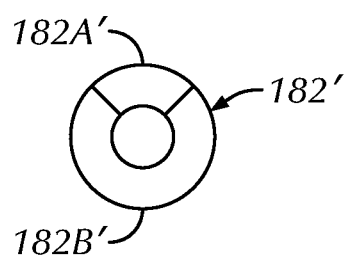

Referring to FIGS. 1 and 2, in some examples, the present subject matter can be used to facilitate insertion of one or more leads 160 into one or more bores 180 within a header 140. That is, as compared to the insertion of leads into typical headers, a physician or other user need not apply a longitudinally-directed force on the one or more leads 160 in order to insert the one or more leads 160 into the header 140. In this way, the number of lead contacts 162 can be increased and/or a size (for instance, diameter, width, or other cross-sectional dimension) of the one or more leads 160 can be decreased from those of a typical lead with a reduced likelihood of damaging the one or more leads 160 during insertion of the one or more leads 160 into the one or more bores 180 of the header 140.

In some examples, the header 140 is a component of an implantable device 100, such as, but not limited to, an implantable stimulation device, an implantable sensing device, and/or an implantable drug delivery device. In some examples, the implantable device 100 includes a housing 102. Within the housing 102, in some examples, are electronics 108. In various examples, the electronics 108 are configured to perform functions and/or operations of the implantable device 100, such as, but not limited to, producing and administering a stimulation pulse, sensing and/or analyzing a physiological parameter, communicating with other devices, administering a drug, or the like. In some examples, the electronics 108 within the housing 102 can also include a battery or other power source and/or a capacitor within the housing 102 for powering of the implantable device 100 and producing the stimulation pulse. The housing 102, in some examples, is hermetically sealed in order to inhibit contaminants, such as body fluid and/or tissue, for instance, from entering the housing 102 and compromising the electronics 108 within the housing 102. In order to electrically couple the electronics 108 within the housing 102 with the header 140, in some examples, a feedthrough 106 is disposed between the electronics 108 within the housing 102 and the header 140, the feedthrough 106 being configured to maintain the hermetic seal of the housing 102 while allowing electrical communication therethrough to enable electrical communication of the electronics 108 within the housing 102 to one or more components outside of the housing 102, such as, but not limited to one or more components within and/or attached to the header 140.

In some examples, the implantable device 100 includes at least one lead 160. In some examples, such as the example shown in FIGS. 1 and 2, the implantable device 100 includes two leads 160. In other examples, however, the implantable device can include more or fewer than two leads, depending upon the application for which the implantable device is being used.

In some examples, the at least one lead 160 is attached to the header 140 of the implantable device 100. As will be described below, the header 140, in some examples, is configured to accept the at least one lead 160 therein to electrically couple the at least one lead 160 to the electronics 108 within the housing 102. In some examples, the at least one lead 160 includes an elongate body 161 with a proximal end 160A and a distal end 160B. In some examples, the at least one lead 160 includes at least one lead contact 162 proximate the proximal end 160A and at least one lead electrode 164 proximate the distal end 160B. In various examples, it should be understood that the lead 160 can include various numbers of lead contacts 162 and lead electrodes 164. For instance, in the example shown in FIGS. 1 and 2, the leads can include eight lead contacts 162 and eight lead electrodes 164. In other examples, however, the leads can include more or fewer than eight lead contacts 162 and eight lead electrodes 164, depending upon the application for which the implantable device is being used. For instance, more than eight lead electrodes could be beneficial for a particular application, such as, but not limited to, neurostimulation. In some examples, the number of lead electrodes 164 corresponds to the number of lead contacts 162, with each lead electrode 164 being electrically coupled to a different lead contact 162 via an electrical conductor running within the elongate body 161 of the lead 160 from the lead contact 162 to the lead electrode 164. In other examples, multiple lead electrodes 164 can be electrically coupled to a single lead contact 162. In still other examples, one lead electrode 164 can be electrically coupled to multiple lead contacts 162. Various numbers of lead contacts 162 and lead electrodes 164, as well as various electrical connections between the lead contacts 162 and the lead electrodes 164 are contemplated herein in various examples, depending upon the application for which the implantable device is to be used 100.

In some examples, the header 140 includes a first header portion 142 and a second header portion 144. In some examples, the second header portion 144 is at least partially disengageable from the first header portion 142. In some examples, the header 140 includes a closed configuration 140A (FIG. 1) in which the first header portion 142 is fully engaged with the second header portion 144. The header 140, in some examples, includes an open configuration 140B (FIG. 2) in which the first header portion 142 is at least partially disengaged from the second header portion 144. That is, in some examples, the header 140 can be opened (placed in the open configuration 140B) to insert the at least one lead 160 within the at least one bore 180 and then closed (placed in the closed configuration 140A) to engage the at least one lead 160 within the at least one bore 180, and, in turn, electrically couple the one or more lead contacts 162 with the electronics 108 within the housing 102, as will be described in more detail below.

In some examples, the first header portion 142 is removably coupled to the second header portion 144, such that the second header portion 144 is fully engaged with the first header portion 142 in the closed configuration 140A and fully disengaged and removed from the first header portion 142 in the open configuration 140B. Although the first and second header portions 142, 144 being completely removable from one another is shown in FIGS. 1 and 2, other configurations to allow the first header portion 142 to be at least partially disengaged from the second header portion 144 are contemplated. For instance, in some examples, the first header portion 142 can be pivotably coupled to the second header portion 144, such that the second header portion 144 is rotatable with respect to the first header portion 142 from being fully engaged with the first header portion 142 in the closed configuration 140A to being partially disengaged from the first header portion 142 in the open configuration. In further examples, the first header portion 142 is pivotably coupled to the second header portion 144 at a hinge H1 or H2. Such a configuration allows the first header portion 142 to pivot relative to the second header portion 144, allowing the header to be selectively placed in either the open configuration or the closed configuration 140A. In some examples, the hinge H1 can be disposed substantially in line but offset from the one or more bores 180. In other examples, the hinge H2 can be disposed substantially perpendicular to the one or more bores 180. In other examples, other hinge locations are contemplated, provided the hinge location allows opening and closing of the header without damaging or compromising the one or more leads or the one or more bores or components of the bores during opening or closing of the header.

In some examples, the first header portion 142 is removably coupled to the second header portion 144 using at least one securement member 152. The securement member 152, in some examples, is a screw or other fastener disposed within a hole or latch 150 within the header 140 which includes a through hole through one of the first and second header portions 142, 144 and a threaded hole within the other of the first and second header portions 142, 144 to allow tightening of the securement member 152 to fasten the first header portion 142 to the second header portion 144. In some examples, the at least one securement member 152 includes an alignment member, such as, but not limited to, a pin. In some examples, a combination of pins and fasteners can be used for the securement members 152, with the one or more pins acting to hold tolerances and the one or more fasteners acting to maintain connection of the first header portion 142 to the second header portion 144. In some examples, the header 140 includes more than one hole (for instance, cylindrical or any shape) 150 and securement member 152 to allow multiple securement points of the first header portion 142 to the second header portion 144. In the example shown in FIGS. 1 and 2, the header includes four securement members 152 and corresponding holes 150 within the header 140, although this is not intended to be limiting as more or fewer than four securement members 152 and corresponding holes 150 within the header 140 are contemplated in other examples.

In some examples, the at least one bore 180 within the header 140 is sized and shaped to accommodate the proximal end 160A of the at least one lead 160. In the example of FIGS. 1 and 2, the header 140 includes two bores 180 in order to accommodate the proximal ends 160A of the two leads 160. However, in other examples, the implantable device can include more or fewer than two bores, depending upon the application for which the implantable device is being used and how many leads are intended to be used with the implantable device.

In some examples, the at least one bore 180 includes a bore opening 181 in a wall 141 of the header 140. In some examples, the at least one bore 180 is disposed along a junction of the first header portion 142 and the second header portion 144, such that part of the at least one bore 180 is disposed within the first header portion 142 and another part of the at least one bore 180 is disposed within the second header portion 144. In some examples, the at least one bore 180 is split substantially longitudinally to form a first bore portion 180A and a second bore portion 180B.

In some examples, the first bore portion 180A forms a first channel 180A disposed within the first header portion 142 and including a first channel opening 143 in a first surface 142A of the first header portion 142 along a length of the first channel 180A. In some examples, the first channel 180A includes a semicircular cross section. In other examples, other cross sections of the first channel are contemplated depending upon the shape of the lead to be inserted within the first channel, such as, but not limited to, semi-elliptical, polygonal-shaped, or the like. In some examples, the first channel opening 143 forms a substantially rectangular opening in the first surface 142A, when viewed from a point perpendicular to the first surface 142A, substantially running the length of the first channel 180A, that allows for the proximal end 160A of the lead 160 to be inserted through the first channel opening 143 and into the first bore portion 180A.

In some examples, the second bore portion 180B forms a second channel 180B disposed within the second header portion 144 and including a second channel opening 145 in a second surface 144A of the second header portion 144 along a length of the second channel 180B. In some examples, the second channel 180B includes a semicircular cross section. In other examples, other cross sections of the second channel are contemplated depending upon the shape of the lead to be inserted within the second channel, such as, but not limited to, semi-elliptical, polygonal-shaped, or the like. In some examples, the second channel opening 145 forms a substantially rectangular opening in the second surface 144A, when viewed from a point perpendicular to the second surface 144A, substantially running the length of the second channel 144A, that allows for the proximal end 160A of the lead 160 to be inserted through the second channel opening 145 and into the second bore portion 180B.

In some examples, with the header 140 in the open configuration 140B, the length of the first bore portion 180A is accessible to allow the lead 160 to be inserted within the first channel 180A through the first channel opening 143. In other examples, with the header 140 in the open configuration 140B, the length of the second bore portion 180B is accessible to allow the lead 160 to be inserted within the second channel 180B through the second channel opening 145. In some examples, with the header 140 in the closed configuration 140A, the first surface 142A of the first header portion 142 abuts the second surface 144A of the second header portion 144 so that the first bore portion 180A and the second bore portion 180B form the bore 180 accessible only through the bore opening 181 in the wall 141 of the header 140, such that, with the proximal end 160A of the lead 160 disposed within the bore 180, the elongate body 161 of the lead 160 extends distally from the bore opening 181.

In some examples, at least one header contact 184 is disposed within the bore 180 and configured to electrically couple to the lead contact 162 with the proximal end 160A of the lead 160 disposed within the bore 180. In some examples, the bore 180 includes more than one header contact 184 within the bore 180. In other examples, the number of header contacts 184 within the bore corresponds to the number of lead contacts 162 of the lead 160. In some examples, the at least one header contact 184 is electrically conductive and electrically coupled to the electronics 108 within the housing 102 via the feedthrough 106. In this way, when the proximal end 160A of the lead 160 is disposed within the bore 180 and one of the lead contacts 162 touches one of the header contacts 184, the lead contact 162 electrically couples with the header contact 184 and, in turn, the lead contact 162, as well as the one or more lead electrodes 164 to which the lead contact 162 is electrically coupled, is electrically coupled to the electronics 108 of the implantable device 100. In some examples, the at least one header contact 184 is disposed within just one of the first and second header portions 142, 144. For instance, in some examples, the at least one header contact 184 is disposed within only the second header portion 144 and the first header portion 142 includes no corresponding header contact. In other examples, the at least one header contact 184 is disposed within only the first header portion 142 and the second header portion 144 includes no corresponding header contact. In still other examples, both the first and second header portions 142, 144 can each include at least one header contact 184.

In some examples, a positioning feature 190 is disposed within the bore 180. In some examples, the positioning feature 190 is configured to interact with a corresponding lead feature 170 proximate the proximal end 160A of the lead 160. With the proximal end 160A of the lead 160 disposed within the bore 180 and the positioning feature 190 interacting with the lead feature 170, in some examples, the at least one lead contact 162 aligns with the at least one header contact 184 to allow the at least one lead contact 162 to electrically couple to the at least one header contact 184. That is, in some examples, the lead feature 170 and the positioning feature 190 are located on the lead 160 and within the bore 180, respectively, to ensure that each of the one or more lead contacts 162 are aligned with the one or more header contacts 184 with the lead 160 positioned within the bore 180 and the positioning feature 190 interacting with the lead feature 170, such that proper electrical connection is made between the one or more header contacts 184 and the corresponding one or more lead contacts 162, thereby providing for proper operation of the one or more lead electrodes 164 by the electronics 108 of the implantable device 100.

In some examples, the positioning feature 190 includes a pin 190 disposed within the bore 180 and the lead feature 170 includes a corresponding hole 170 of any shape within the lead 160 proximate the proximal end 160A of the lead 160. In some examples, the hole 170 is complementary to the pin 190, such that, with the proximal end 160A of the lead 160 disposed within the bore 180 and the pin 190 disposed within the hole 170 of the lead 160, the lead 160 is positioned within the bore 180 to allow the at least one lead contact 162 to align with and electrically couple to the at least one header contact 184. Although the positioning feature 190 of the bore 180 is shown in FIG. 2 as a pin 190 and the lead feature 170 is shown as a corresponding hole 170 in the present examples, it is contemplated, in other examples, that the positioning feature 190 of the bore 180 includes a hole and the lead feature 170 includes a corresponding pin or that each of the positioning feature 190 and the lead feature 170 includes at least a pin and a hole or another combination of protrusions, bumps, notches, grooves, or the like, such that the positioning feature(s) and the lead feature(s) interact with each other to facilitate proper placement and/or alignment of the one or more leads 160 within the one or more bores 180.

Referring now to FIGS. 1-3B, in some examples, the implantable device 100 includes a seal member 182 including a first seal portion 182A disposed within the first bore portion 180A of the first header portion 142 and a second seal portion 182B disposed within the second bore portion 180B of the second header portion 144, wherein, with the header 140 in the closed configuration 140A and the proximal end 160A of the lead 160 within the bore 180, the first seal portion 182A abuts the second seal portion 182B and the first seal portion 182A and the second seal portion 182B extends into the bore 180 to abut the elongate body 161 of the lead 160. In some examples, the seal member 182 is formed at least partially from silicone and/or another insulative polymer. In this way, the seal member 182 creates a seal against the lead 160 to inhibit foreign material from getting past the seal member 182 and, for instance, contaminating an interior of the bore 180 and/or the header 140, or creating a short across lead contacts 162 or header contacts 184. In some examples, a seal member 182 is disposed between each header contact 184 and at the bore opening 181 to inhibit foreign material (like, for instance, bodily fluid) from entering the bore 180 and from infiltrating multiple header contacts 184, thereby reducing the likelihood of creating a short between header contacts 184, causing a malfunction of the implantable device 100, and/or damaging the implantable device 100.

In some examples, as shown in FIGS. 1-3A, the first seal portion 182A and the second seal portion 182B each respectively extend substantially halfway around the bore 180 meeting along a centerline of the seal member 182. However, in other examples, such as that which is shown in FIG. 3B, depending upon the design of the first and second header portions, a seal member 182' can include a first seal portion 182A' that extends around less of the bore than a second seal portion 182B'. With such a configuration, the first and second seal portions 182A', 182B' can still abut one another with the header in the closed configuration in order to form a seal around a lead within the bore.

In some examples, with the first header portion 142 and the second header portion 144 properly aligned (using the one or more securement members 152 and/or geometry of the first and second surfaces 142A, 144A to properly align the first and second header portions 142, 144) in the closed configuration 140A, the one or more bores 180 are aligned. With the first and second header portions 142, 144 properly aligned, in some examples, the first and second seal portions 182A, 182B are aligned with one another and the one or more header contacts 184 are properly situated and aligned to allow the one or more leads 160 to be inserted within the one or more bores 180 with the one or more header contacts 184 aligning with the corresponding one or more lead contacts 162 and the seal members 182 being properly situated to insulate the lead and header contacts 162, 184 for proper functioning of the implantable device 100.

Figure 4:
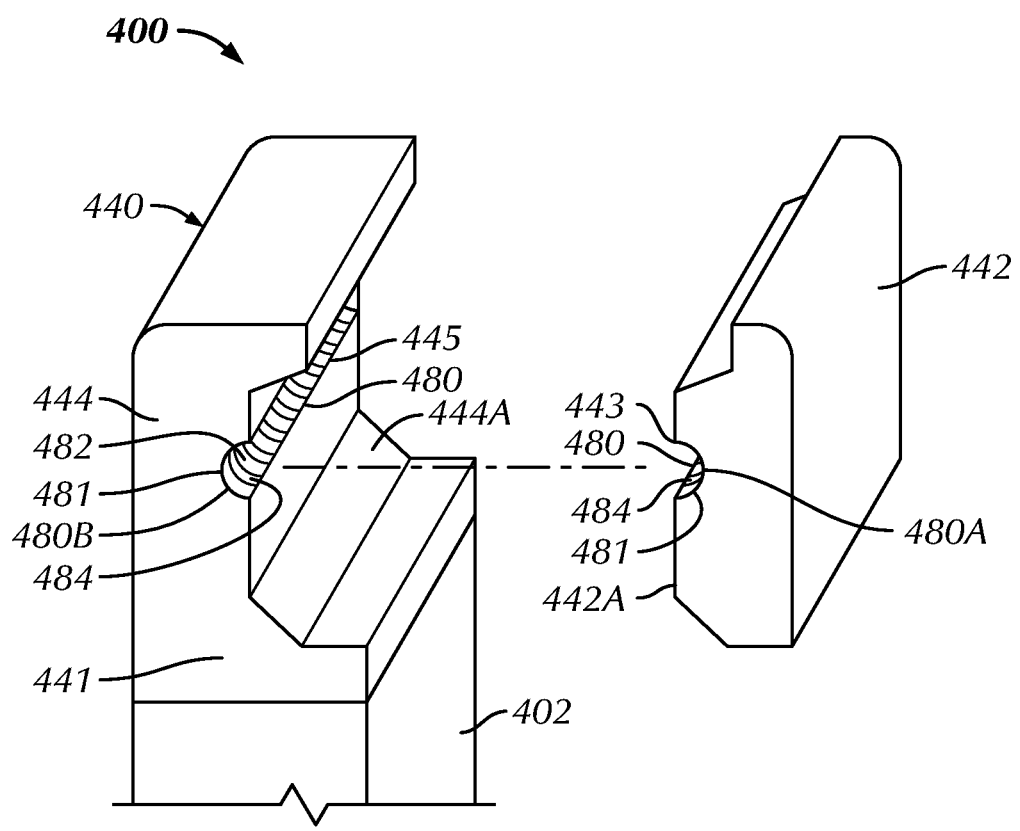
FIG. 4 is a perspective view of an implantable medical device header in accordance with at least one example of the invention.

Referring now to FIG. 4, an implantable device 400 is similar to the implantable device 100 described above. In some examples, the implantable device 400 includes a header 440 coupled to a housing 402. Within the housing 402, in some examples, are electronics configured to allow the implantable device 400 to function in its intended capacity, communicate with other devices, and the like. In some examples, the electronics within the housing 402 can also include a battery or other power source and/or a capacitor within the housing 402 for powering of the implantable device 400 and producing the stimulation pulse. The housing 402, in some examples, is hermetically sealed in order to inhibit contaminants, such as body fluid and/or tissue, for instance, from entering the housing 402 and compromising the electronics within the housing 402.

In some examples, the implantable device 400 includes at least one lead. In the example shown in FIG. 4, the header 440 includes one bore 480 to accept one lead. However, in other examples, the header can include more than one bore to include multiple leads.

In some examples, the at least one lead is attached to the header 440 of the implantable device 400. The header 440, in some examples, is configured to accept the at least one lead therein to electrically couple the at least one lead to the electronics within the housing 402. In some examples, the at least one lead is similar to the lead 160 described above with respect to the implantable device 100.

In some examples, the header 440 includes a first header portion 442 and a second header portion 444. In some examples, the second header portion 444 is at least partially disengageable from the first header portion 442. In some examples, the header 440 includes a closed configuration similar to the closed configuration 140A described above with respect to the implantable device 100, in which the first header portion 442 is fully engaged with the second header portion 444. The header 440, in some examples, includes an open configuration similar to the open configuration 140B described above with respect to the implantable device 100, in which the first header portion 442 is at least partially disengaged from the second header portion 444. That is, in some examples, the header 440 can be opened (placed in the open configuration) to insert the at least one lead within the at least one bore 480 and then closed (placed in the closed configuration) to engage the at least one lead within the at least one bore 480, and, in turn, electrically couple the one or more lead contacts with the electronics within the housing 402.

In some examples, the first header portion 442 is removably coupled to the second header portion 444, such that the second header portion 444 is fully engaged with the first header portion 442 in the closed configuration and fully disengaged and removed from the first header portion 442 in the open configuration. Although the first and second header portions 442, 444 being completely removable from one another is shown in FIG. 4, other configurations to allow the first header portion 442 to be at least partially disengaged from the second header portion 444 are contemplated. For instance, in some examples, the first header portion 442 can be pivotably coupled to the second header portion 444, such that the second header portion 444 is rotatable with respect to the first header portion 442 from being fully engaged with the first header portion 442 in the closed configuration to being partially disengaged from the first header portion 442 in the open configuration. In further examples, the first header portion 442 is pivotably coupled to the second header portion 444 at a hinge. Such a configuration allows the first header portion 442 to pivot relative to the second header portion 444, allowing the header to be selectively placed in either the open configuration or the closed configuration.

In some examples, the first header portion 442 is removably coupled to the second header portion 444 using at least one securement member. The securement member, in some examples, is a screw, latch, or other fastener disposed within a hole within the header 440 which includes a through hole through one of the first and second header portions 442, 444 and a threaded hole within the other of the first and second header portions 442, 444 to allow tightening of the securement member to fasten the first header portion 442 to the second header portion 444. In some examples, the header 440 includes more than one hole in any shape and more than one securement member to allow multiple securement points of the first header portion 442 to the second header portion 444. The multiple securement points and holes, in some examples, can include different shapes that would only allow the first header portion 442 and the second header portion 444 to engage in a unique position.

In some examples, the at least one bore 480 includes a bore opening 481 in a wall 441 of the header 440. In some examples, the at least one bore 480 is disposed along a junction of the first header portion 442 and the second header portion 444, such that part of the at least one bore 480 is disposed within the first header portion 442 and another part of the at least one bore 480 is disposed within the second header portion 444. In some examples, the at least one bore 480 is split substantially longitudinally to form a first bore portion 480A and a second bore portion 480B.

In some examples, the first bore portion 480A forms a first channel 480A disposed within the first header portion 442 and including a first channel opening 443 in a first surface 442A of the first header portion 442 along a length of the first channel 480A. In some examples, the first channel 480A includes a semicircular cross section. In other examples, other cross sections of the first channel are contemplated depending upon the shape of the lead to be inserted within the first channel, such as, but not limited to, semi-elliptical, polygonal-shaped, or the like. In some examples, the first channel opening 443 forms a substantially rectangular opening in the first surface 442A, when viewed from a point perpendicular to the first surface 442A, substantially running the length of the first channel 480A, that allows for the proximal end of the lead to be inserted through the first channel opening 443 and into the first bore portion 480A.

In some examples, the second bore portion 480B forms a second channel 480B disposed within the second header portion 444 and including a second channel opening 445 in a second surface 444A of the second header portion 444 along a length of the second channel 480B. In some examples, the second channel 480B includes a semicircular cross section. In other examples, other cross sections of the second channel are contemplated depending upon the shape of the lead to be inserted within the second channel, such as, but not limited to, semi-elliptical, polygonal-shaped, or the like. In some examples, the second channel opening 445 forms a substantially rectangular opening in the second surface 444A, when viewed from a point perpendicular to the second surface 444A, substantially running the length of the second channel 444A, that allows for the proximal end of the lead to be inserted through the second channel opening 445 and into the second bore portion 480B.

In some examples, with the header 440 in the open configuration, the length of the first bore portion 480A is accessible to allow the lead to be inserted within the first channel 480A through the first channel opening 443. In other examples, with the header 440 in the open configuration, the length of the second bore portion 480B is accessible to allow the lead to be inserted within the second channel 480B through the second channel opening 445. In some examples, with the header 440 in the closed configuration, the first surface 442A of the first header portion 442 abuts the second surface 444A of the second header portion 444 so that the first bore portion 480A and the second bore portion 480B form the bore 480 accessible only through the bore opening 481 in the wall 441 of the header 440, such that, with the proximal end of the lead disposed within the bore 480, the elongate body of the lead extends distally from the bore opening 481.

In some examples, at least one header contact 484 is disposed within the bore 480 and configured to electrically couple to the lead contact with the proximal end of the lead disposed within the bore 480. In some examples, the bore 480 includes more than one header contact 484 within the bore 480. In other examples, the number of header contacts 484 within the bore corresponds to the number of lead contacts of the lead. In some examples, the at least one header contact 484 is electrically conductive and electrically coupled to the electronics within the housing 402 via a feedthrough similar to the feedthrough 106 of the implantable device 100 described above. In this way, when the proximal end of the lead is disposed within the bore 480 and one of the lead contacts touches one of the header contacts 484, the lead contact electrically couples with the header contact 484 and, in turn, the lead contact, as well as the one or more lead electrodes to which the lead contact is electrically coupled, is electrically coupled to the electronics of the implantable device 400. In some examples, the at least one header contact 484 is disposed within just one of the first and second header portions 442, 444. For instance, in some examples, the at least one header contact 484 is disposed within only the second header portion 444 and the first header portion 442 includes no corresponding header contact. In other examples, the at least one header contact 484 is disposed within only the first header portion 442 and the second header portion 444 includes no corresponding header contact. In still other examples, both the first and second header portions 442, 444 can each include at least one header contact 484.

In some examples, the first header portion 442 forms a side of the header 440 and moves laterally with respect to the second header portion 444 between the closed configuration to the open configuration. In some examples, the first and second header portions 442, 444 include self-aligning features to ensure proper positioning of the first header portion 442 with respect to the second header portion 444. The first surface 442A and the second surface 444A, in some examples, include mating geometries that allow proper positioning of the first and second header portions 442, 444, such that the first bore portion 480A and the second bore portion 480B align correctly with one another to properly form the at least one bore 480. In the example shown in FIG. 4, the mating geometries of the first surface 442A and the second surface 444A form angles and flats which allow the first header portion 442 to be inserted into the header 440 and abutting the second header portion 444 in the proper orientation and inhibit the first header portion 442 from being inserted into the header 440 in a different, improper orientation, such as, for instance, inverted from what is shown in FIG. 4.

In some examples, a positioning feature (for instance, similar to the positioning feature 190 of the implantable device 100 described above or the further examples of positioning features described below) is disposed within the bore 480. In some examples, the positioning feature is configured to interact with a corresponding lead feature proximate the proximal end of the lead. With the proximal end of the lead disposed within the bore 480 and the positioning feature interacting with the lead feature, in some examples, the at least one lead contact aligns with the at least one header contact 484 to allow the at least one lead contact to electrically couple to the at least one header contact 484. That is, in some examples, the lead feature and the positioning feature are located on the lead and within the bore 480, respectively, to ensure that each of the one or more lead contacts are aligned with the one or more header contacts 484 with the lead positioned within the bore 480 and the positioning feature interacting with the lead feature, such that proper electrical connection is made between the one or more header contacts 484 and the corresponding one or more lead contacts, thereby providing for proper operation of the one or more lead electrodes by the electronics of the implantable device 400.

In some examples, the implantable device 400 includes a seal member 482 including a first seal portion disposed within the first bore portion 480A of the first header portion 442 and a second seal portion disposed within the second bore portion 480B of the second header portion 444, wherein, with the header 440 in the closed configuration and the proximal end of the lead within the bore 480, the first seal portion abuts the second seal portion and the first seal portion and the second seal portion extends into the bore 480 to abut the elongate body of the lead. In this way, the seal member 482 creates a seal against the lead to inhibit foreign material from getting past the seal member 482 and, for instance, contaminating an interior of the bore 480 and/or the header 440, or creating a short across lead contacts or header contacts 484. In some examples, a seal member 482 is disposed between each header contact 484 and at the bore opening 481 to inhibit foreign material (like, for instance, bodily fluid) from entering the bore 480 and from infiltrating multiple header contacts 484, thereby reducing the likelihood of creating a short between header contacts 484, causing a malfunction of the implantable device 400, and/or damaging the implantable device 400.

In some examples, with the first header portion 442 and the second header portion 444 properly aligned (using the one or more securement members and/or geometry of the first and second surfaces 442A, 444A to properly align the first and second header portions 442, 444) in the closed configuration, the one or more bores 480 are aligned. With the first and second header portions 442, 444 properly aligned, in some examples, the first and second seal portions are aligned with one another and the one or more header contacts 484 are properly situated and aligned to allow the one or more leads to be inserted within the one or more bores 480 with the one or more header contacts 484 aligning with the corresponding one or more lead contacts and the seal members 482 being properly situated to insulate the lead and header contacts 484 for proper functioning of the implantable device 400.

Figure 5:
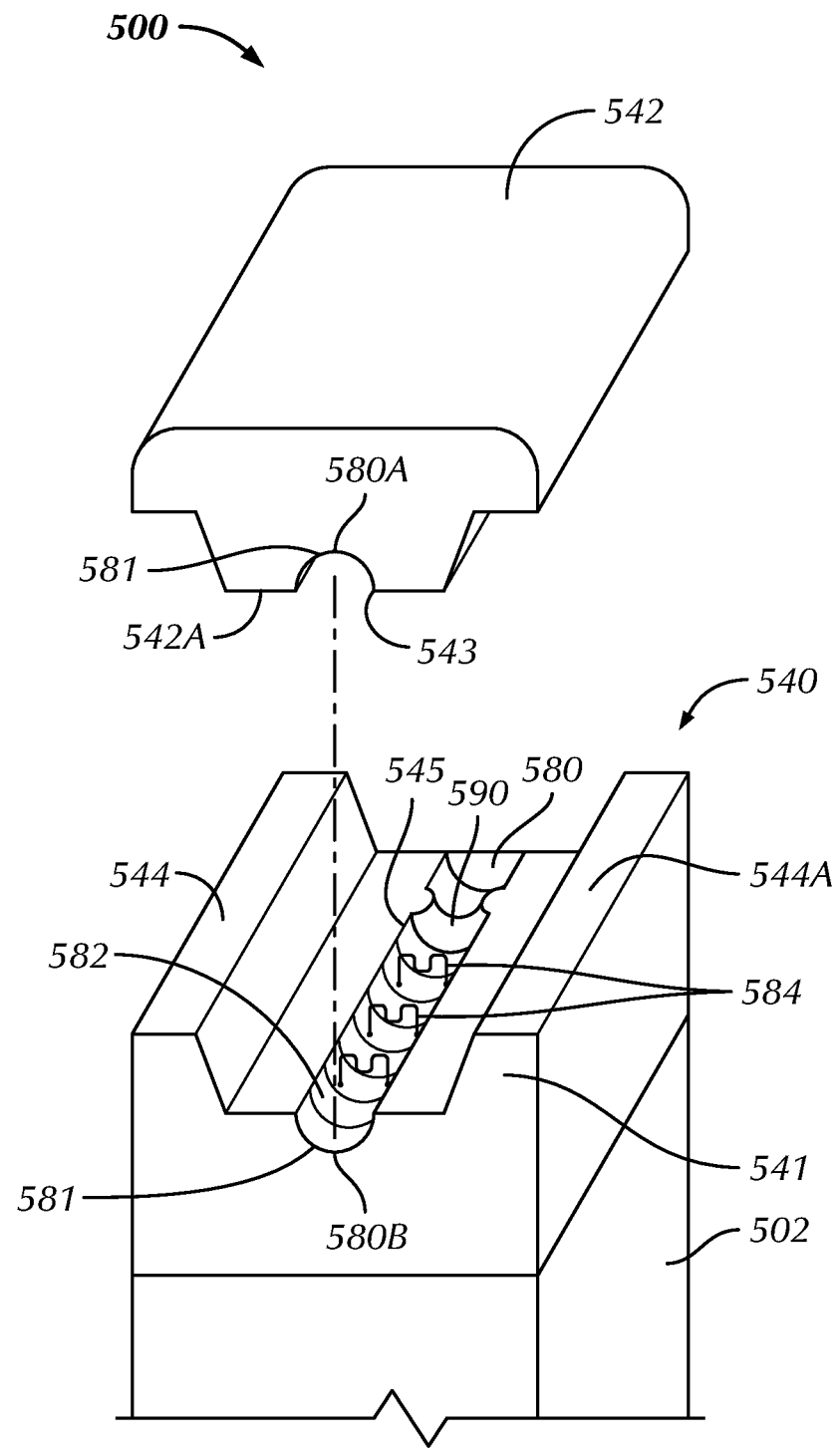
FIG. 5 is a perspective view of an implantable medical device header in accordance with at least one example of the invention.

Referring now to FIG. 5, an implantable device 500 is similar to the implantable devices 100, 400 described above. In some examples, the implantable device 500 includes a header 540 coupled to a housing 502. Within the housing 502, in some examples, are electronics configured to allow the implantable device 500 to function in its intended capacity, communicate with other devices, and the like. In some examples, the electronics within the housing 502 can also include a battery or other power source and/or a capacitor within the housing 502 for powering of the implantable device 500 and producing the stimulation pulse. The housing 502, in some examples, is hermetically sealed in order to inhibit contaminants, such as body fluid and/or tissue, for instance, from entering the housing 502 and compromising the electronics within the housing 502.

In some examples, the implantable device 500 includes at least one lead. In the example shown in FIG. 5, the header 540 includes one bore 580 to accept one lead. However, in other examples, the header can include more than one bore to include multiple leads.

In some examples, the at least one lead is attached to the header 540 of the implantable device 500. The header 540, in some examples, is configured to accept the at least one lead therein to electrically couple the at least one lead to the electronics within the housing 502. In some examples, the at least one lead is similar to the lead 160 described above with respect to the implantable device 100.

In some examples, the header 540 includes a first header portion 542 and a second header portion 544. In some examples, the second header portion 544 is at least partially disengageable from the first header portion 542. In some examples, the header 540 includes a closed configuration similar to the closed configuration 140A described above with respect to the implantable device 100, in which the first header portion 542 is fully engaged with the second header portion 544. The header 540, in some examples, includes an open configuration similar to the open configuration 140B described above with respect to the implantable device 100, in which the first header portion 542 is at least partially disengaged from the second header portion 544. That is, in some examples, the header 540 can be opened (placed in the open configuration) to insert the at least one lead within the at least one bore 580 and then closed (placed in the closed configuration) to engage the at least one lead within the at least one bore 580, and, in turn, electrically couple the one or more lead contacts with the electronics within the housing 502.

In some examples, the first header portion 542 is removably coupled to the second header portion 544, such that the second header portion 544 is fully engaged with the first header portion 542 in the closed configuration and fully disengaged and removed from the first header portion 542 in the open configuration. Although the first and second header portions 542, 544 being completely removable from one another is shown in FIG. 5, other configurations to allow the first header portion 542 to be at least partially disengaged from the second header portion 544 are contemplated. For instance, in some examples, the first header portion 542 can be pivotably coupled to the second header portion 544, such that the second header portion 544 is rotatable with respect to the first header portion 542 from being fully engaged with the first header portion 542 in the closed configuration to being partially disengaged from the first header portion 542 in the open configuration. In further examples, the first header portion 542 is pivotably coupled to the second header portion 544 at a hinge. Such a configuration allows the first header portion 542 to pivot relative to the second header portion 544, allowing the header to be selectively placed in either the open configuration or the closed configuration.

In some examples, the first header portion 542 is removably coupled to the second header portion 544 using at least one securement member. The securement member, in some examples, is a screw or other fastener disposed within a hole within the header 540 which includes a through hole through one of the first and second header portions 542, 544 and a threaded hole within the other of the first and second header portions 542, 544 to allow tightening of the securement member to fasten the first header portion 542 to the second header portion 544. In some examples, the header 540 includes more than one hole and securement member to allow multiple securement points of the first header portion 542 to the second header portion 544.

In some examples, the at least one bore 580 includes a bore opening 581 in a wall 541 of the header 540. In some examples, the at least one bore 580 is disposed along a junction of the first header portion 542 and the second header portion 544, such that part of the at least one bore 480 is disposed within the first header portion 542 and another part of the at least one bore 580 is disposed within the second header portion 544. In some examples, the at least one bore 580 is split substantially longitudinally to form a first bore portion 580A and a second bore portion 580B.

In some examples, the first bore portion 580A forms a first channel 580A disposed within the first header portion 542 and including a first channel opening 543 in a first surface 542A of the first header portion 542 along a length of the first channel 580A. In some examples, the first channel 580A includes a semicircular cross section. In other examples, other cross sections of the first channel are contemplated depending upon the shape of the lead to be inserted within the first channel, such as, but not limited to, semi-elliptical, polygonal-shaped, or the like. In some examples, the first channel opening 543 forms a substantially rectangular opening in the first surface 542A, when viewed from a point perpendicular to the first surface 542A, substantially running the length of the first channel 580A, that allows for the proximal end of the lead to be inserted through the first channel opening 543 and into the first bore portion 580A.

In some examples, the second bore portion 580B forms a second channel 580B disposed within the second header portion 544 and including a second channel opening 545 in a second surface 544A of the second header portion 544 along a length of the second channel 580B. In some examples, the second channel 580B includes a semicircular cross section. In other examples, other cross sections of the second channel are contemplated depending upon the shape of the lead to be inserted within the second channel, such as, but not limited to, semi-elliptical, polygonal-shaped, or the like. In some examples, the second channel opening 545 forms a substantially rectangular opening in the second surface 544A, when viewed from a point perpendicular to the second surface 544A, substantially running the length of the second channel 544A, that allows for the proximal end of the lead to be inserted through the second channel opening 545 and into the second bore portion 580B.

In some examples, with the header 540 in the open configuration, the length of the first bore portion 580A is accessible to allow the lead to be inserted within the first channel 580A through the first channel opening 543. In other examples, with the header 540 in the open configuration, the length of the second bore portion 580B is accessible to allow the lead to be inserted within the second channel 580B through the second channel opening 545. In some examples, with the header 540 in the closed configuration, the first surface 542A of the first header portion 542 abuts the second surface 544A of the second header portion 544 so that the first bore portion 580A and the second bore portion 580B form the bore 580 accessible only through the bore opening 581 in the wall 541 of the header 540, such that, with the proximal end of the lead disposed within the bore 580, the elongate body of the lead extends distally from the bore opening 581.

In some examples, at least one header contact 584 is disposed within the bore 580 and configured to electrically couple to the lead contact with the proximal end of the lead disposed within the bore 580. In some examples, the bore 580 includes more than one header contact 584 within the bore 580. In other examples, the number of header contacts 584 within the bore corresponds to the number of lead contacts of the lead. In some examples, the at least one header contact 584 is electrically conductive and electrically coupled to the electronics within the housing 502 via a feedthrough similar to the feedthrough 106 of the implantable device 100 described above. In this way, when the proximal end of the lead is disposed within the bore 580 and one of the lead contacts touches one of the header contacts 584, the lead contact electrically couples with the header contact 584 and, in turn, the lead contact, as well as the one or more lead electrodes to which the lead contact is electrically coupled, is electrically coupled to the electronics of the implantable device 500. In some examples, the at least one header contact 584 is disposed within just one of the first and second header portions 542, 544. For instance, in some examples, the at least one header contact 584 is disposed within only the second header portion 544 and the first header portion 542 includes no corresponding header contact. In other examples, the at least one header contact 584 is disposed within only the first header portion 542 and the second header portion 544 includes no corresponding header contact. In still other examples, both the first and second header portions 542, 544 can each include at least one header contact 584.

In some examples, the first header portion 542 forms a top of the header 540 and moves vertically with respect to the second header portion 544 between the closed configuration to the open configuration. In some examples, the first and second header portions 542, 544 include self-aligning features to ensure proper positioning of the first header portion 542 with respect to the second header portion 544. The first surface 542A and the second surface 544A, in some examples, include mating geometries that allow proper positioning of the first and second header portions 542, 544, such that the first bore portion 580A and the second bore portion 580B align correctly with one another to properly form the at least one bore 580. In the example shown in FIG. 5, the mating geometries of the first surface 542A and the second surface 544A form angles and flats which allow the first header portion 542 to be inserted into the header 540 and abutting the second header portion 544 in the proper orientation and inhibit the first header portion 542 from being inserted into the header 540 in a different, improper orientation.

In some examples, a positioning feature 590 is disposed within the bore 580. In some examples, the positioning feature 590 is configured to interact with a corresponding lead feature proximate the proximal end of the lead. With the proximal end of the lead disposed within the bore 580 and the positioning feature interacting with the lead feature, in some examples, the at least one lead contact aligns with the at least one header contact 584 to allow the at least one lead contact to electrically couple to the at least one header contact 584. That is, in some examples, the lead feature and the positioning feature 590 are located on the lead and within the bore 580, respectively, to ensure that each of the one or more lead contacts are aligned with the one or more header contacts 584 with the lead positioned within the bore 580 and the positioning feature 590 interacting with the lead feature, such that proper electrical connection is made between the one or more header contacts 584 and the corresponding one or more lead contacts, thereby providing for proper operation of the one or more lead electrodes by the electronics of the implantable device 500.

The positioning feature 590, in some examples, includes a protrusion 590 disposed within the bore 580 and the lead feature includes a corresponding indentation within the lead proximate the proximal end of the lead. In some examples, the indentation is complementary to the protrusion 590, such that, with the proximal end of the lead disposed within the bore 580 and the protrusion 590 disposed within the indentation of the lead, the lead is positioned within the bore 580 to allow the at least one lead contact to align with and electrically couple to the at least one header contact 584. In some examples, the protrusion 590 includes a bump 590 extending into the bore 580 and the indentation includes a notch within the lead. In further examples, the protrusion 590 includes one or more radially-extending bumps 590 extending into and disposed at least partially around the bore 580 and the indentation includes a groove disposed within and extending at least partially radially around the lead. In still further examples, the protrusion 590 includes a radially-extending bump 590 extending into and disposed completely around the bore 580 and the indentation includes a groove disposed within and extending completely radially around the lead. Such a configuration can allow rotation of the lead within the bore 580, if desired. In other examples, another positioning feature and mating lead feature can be used. For instance, the positioning feature within the bore 580 can include an indentation and the lead feature on the one or more leads can include a corresponding protrusion to facilitate alignment of the one or more leads within the one or more bores. In other examples, that each of the positioning feature 590 of the bore 580 and the lead feature of the lead includes at least an indentation and a protrusion or another combination of protrusions, bumps, notches, grooves, or the like, such that the positioning feature(s) and the lead feature(s) interact with each other to facilitate proper placement and/or alignment of the one or more leads within the one or more bores 580.

In some examples, the implantable device 500 includes a seal member 582 including a first seal portion disposed within the first bore portion 580A of the first header portion 542 and a second seal portion disposed within the second bore portion 580B of the second header portion 544, wherein, with the header 540 in the closed configuration and the proximal end of the lead within the bore 580, the first seal portion abuts the second seal portion and the first seal portion and the second seal portion extends into the bore 580 to abut the elongate body of the lead. In this way, the seal member 582 creates a seal against the lead to inhibit foreign material from getting past the seal member 582 and, for instance, contaminating an interior of the bore 580 and/or the header 540, or creating a short across lead contacts or header contacts 584. In some examples, a seal member 582 is disposed between each header contact 584 and at the bore opening 581 to inhibit foreign material (like, for instance, bodily fluid) from entering the bore 580 and from infiltrating multiple header contacts 584, thereby reducing the likelihood of creating a short between header contacts 584, causing a malfunction of the implantable device 500, and/or damaging the implantable device 500.

In some examples, with the first header portion 542 and the second header portion 544 properly aligned (using the one or more securement members and/or geometry of the first and second surfaces 542A, 544A to properly align the first and second header portions 542, 544) in the closed configuration, the one or more bores 580 are aligned. With the first and second header portions 542, 544 properly aligned, in some examples, the first and second seal portions are aligned with one another and the one or more header contacts 584 are properly situated and aligned to allow the one or more leads to be inserted within the one or more bores 580 with the one or more header contacts 584 aligning with the corresponding one or more lead contacts and the seal members 582 being properly situated to insulate the lead and header contacts 584 for proper functioning of the implantable device 500.

Figure 6:
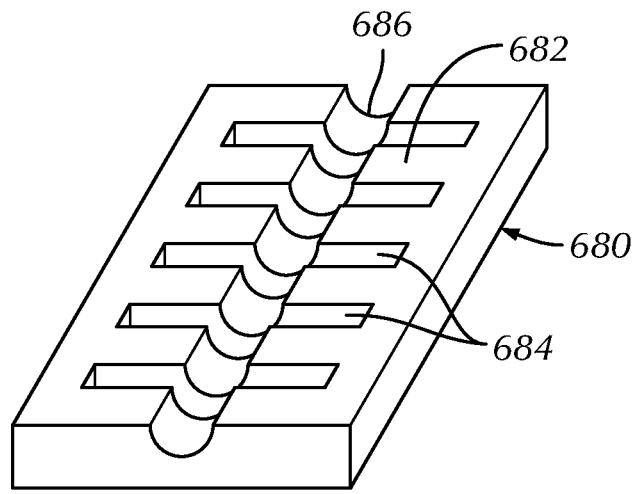
FIG. 6 is a perspective view of a seal member of an implantable medical device header in accordance with at least one example of the invention.

Referring to FIG. 6, in some examples, multiple seal members (such as, for instance, the seal members 182, 482, 582 described above) can be formed in a seal component 680. The seal component 680, in some examples, includes two or more seal ribs 682 spaced from one another with one or more voids 684. In some examples, the seal component 680 can include a groove 686 within the two or more seal ribs 682 in order to be disposed along the bore (such as, for instance, the bores 180, 480, 580 described above) to accept the lead (such as, for instance, the lead 160 described above). In some examples, the seal component 680 is formed from a resilient, insulative material capable of electrical insulation and deformation around an object (such as, for instance, the lead) abutting against the seal component 680 to allow the formation of a seal against the object. In some examples, the seal component 680 is formed from silicone, although, in other examples, the seal component 680 can be formed from other materials instead of, or in addition to, silicone. In other examples, other resilient, insulative materials are contemplated for the formation of the seal component 680, such as, for instance, various other polymers.

In this way, in some examples, a first seal component 680 can be disposed within the first header portion (such as, for instance, the first header portions 142, 442, 542 described above) along the bore with one or more header contacts (such as, for instance, the header contacts 184, 484, 584 described above) extending through the one or voids 684 of the seal component 680, and a second seal component 680 can be disposed within the second header portion (such as, for instance, the second header portions 144, 444, 544 described above) along the bore with one or more header contacts extending through the one or voids 684 of the seal component 680. In this way, the seal component 680 can facilitate manufacturing of the header (such as, for instance, the headers 140, 440, 540 described above) and the one or more bores disposed within the header.

Figure 7:
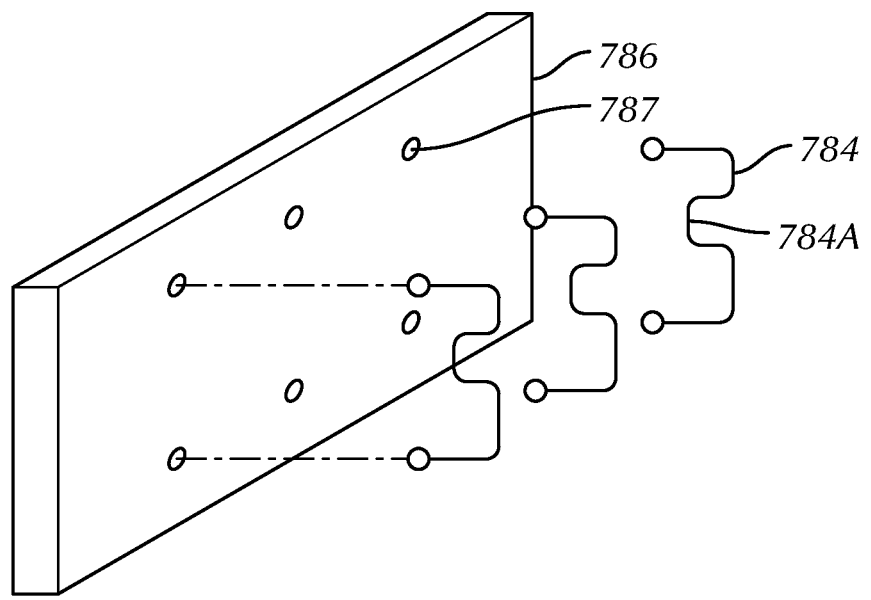
FIG. 7 is a perspective view of header contacts of an implantable medical device header in accordance with at least one example of the invention.
Figure 8:
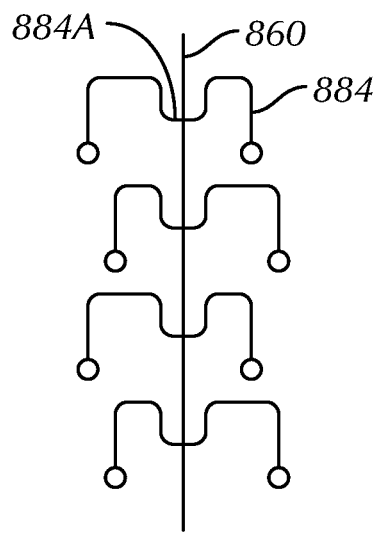
FIG. 8 is a top view of header contacts of an implantable medical device header in accordance with at least one example of the invention.

Referring to FIGS. 7 and 8, in some examples, one or more header contacts 784, 884 can be formed from preformed metal wire. In some examples, the header contacts 784 are attached to a substrate 786, for instance, at connection points 787 in the substrate 786. In some examples, the connection points 787 can be formed within holes in the substrate 786 to allow insertion of the ends of the preformed metal wire of the header contacts 784 therein for additional strength and robustness of the mechanical connection between the one or more header contacts 784 and the substrate 786. The connection points 787, in some examples, are coupled to conductors within the header (such as, for instance, the headers 140, 440, 540 described above) that are routed down to the electronics within the housing (such as, for instance, the housings 102, 402, 502 described above). Each of the header contacts 784, 884, in some examples, include two connection points 787.

In some examples, the one or more header contacts 784, 884 include formed curves 784A, 884A configured to reside within the bore (such as, for instance, the bores 180, 480, 580 described above) and accept a lead 860 (or the lead 160 described above) and electrically couple to one or more lead contacts (such as, for instance, the lead contacts 162 described above). In the example shown in FIG. 7, the header contacts 784 are aligned along the substrate 786. In the example shown in FIG. 8, the header contacts 884 are offset from one another, although the formed curves 884A are aligned in order to reside within the bore and accept the lead 860 therein. In some examples, the header contacts 784, 884 can be formed from one or more conductive metals, such as, but not limited to, platinum, platinum alloys, gold, MP35N, stainless steel, or the like. In some examples, the substrate 786 can be formed from a ceramic material or any other non-conductive material. In some examples, the header contacts 784 coupled to the substrate 786 can be used in conjunction with the sealing component 680 of FIG. 6, such that the header contacts 784 are placed through the voids 684 with the formed curves 784A being aligned with the groove 686 within the sealing component 680, thereby forming the bore within the header.

Figure 9:
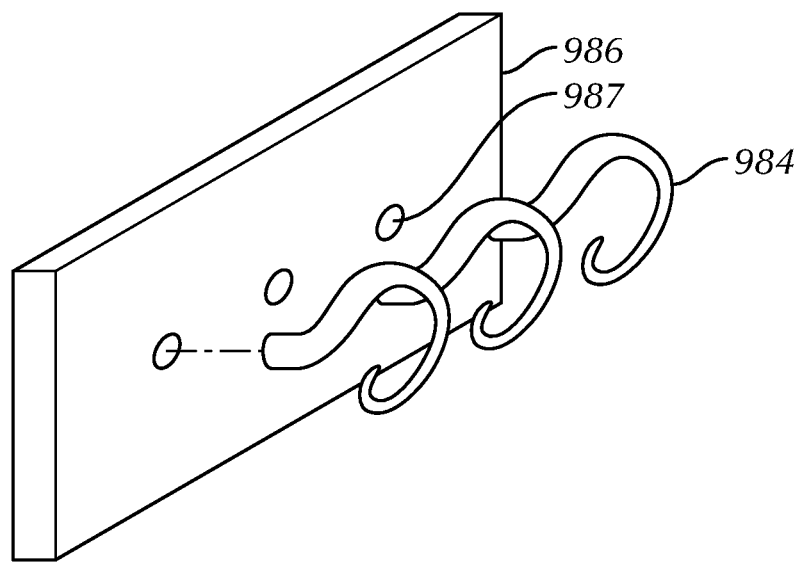
FIG. 9 is a perspective view of header contacts of an implantable medical device header in accordance with at least one example of the invention.
Figure 10:
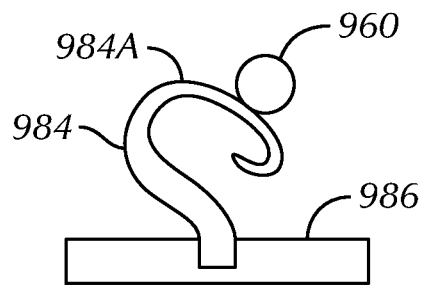
FIG. 10 is a side view of a header contact of an implantable medical device header in accordance with at least one example of the invention.

Referring to FIGS. 9 and 10, in some examples, one or more header contacts 984 can be formed from preformed metal wire or stamped parts. In some examples, the header contacts 984 are attached to a substrate 986, for instance, at a connection point 987 in the substrate 986. In some examples, the connection point 987 can be formed within a hole in the substrate 986 to allow insertion of the end of the preformed metal wire of the header contact 984 therein for additional strength and robustness of the mechanical connection between the one or more header contacts 984 and the substrate 986. The connection points 987, in some examples, are coupled to conductors within the header (such as, for instance, the headers 140, 440, 540 described above) that are routed down to the electronics within the housing (such as, for instance, the housings 102, 402, 502 described above). Each of the header contacts 984, in some examples, include one connection points 987.

In some examples, the one or more header contacts 984 include formed curves 984A configured to reside within the bore (such as, for instance, the bores 180, 480, 580 described above) to accept a lead 960 (or the lead 160 described above) and electrically couple to one or more lead contacts (such as, for instance, the lead contacts 162 described above). In some examples, the one or more header contacts 984 are formed into hooks with the formed curve 984A being configured to contact the lead contact of the lead 960. The hook shape of the header contact 984 in this example allows for the header contact 984 to flex against the lead 960 and ensure good contact with the lead contact of the lead 960 and, in turn, ensure a proper electrical connection. In some examples, the header contacts 984 can be formed from one or more conductive metals, such as, but not limited to, platinum, platinum alloys, gold, MP35N, stainless steel, or the like. In some examples, the substrate 986 can be formed from a ceramic material. In some examples, the header contacts 984 coupled to the substrate 986 can be used in conjunction with the sealing component 680 of FIG. 6, such that the header contacts 984 are placed through the voids 684 with the formed curves 984A being aligned with the groove 686 within the sealing component 680, thereby forming the bore within the header.

Figure 11:
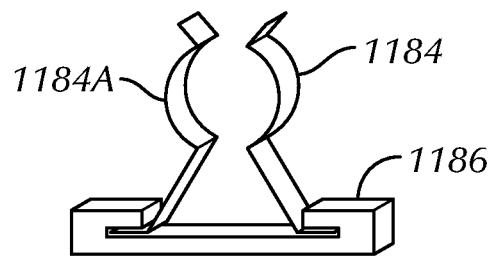
FIG. 11 is a perspective view of a header contact of an implantable medical device header in accordance with at least one example of the invention.

Referring to FIG. 11, in some examples, one or more header contacts 1184 can be formed from spring metal to form one or more spring contacts. In some examples, the header contacts 1184 are attached to a base 1186. The one or more header contacts 1184, in some examples, are coupled to conductors within the header (such as, for instance, the headers 140, 440, 540 described above) that are routed down to the electronics within the housing (such as, for instance, the housings 102, 402, 502 described above).

In some examples, the one or more header contacts 1184 include formed curves 1184A configured to reside within the bore (such as, for instance, the bores 180, 480, 580 described above) to accept a lead (such as, for instance, the lead 160 described above) and electrically couple to one or more lead contacts (such as, for instance, the lead contacts 162 described above). In some examples, each header contact 1184 includes one or more pieces of spring metal formed into a shape to accept the lead therein, with the two pieces of the header contact 1184 spaced slightly to allow placement of the lead between the two pieces of the header contact 1184 such that they flex apart and allow the lead to pass into and reside within the area within the formed curves 1184A of each of the pieces of the header contact 1184. In some examples, each header contact 1184 includes two pieces of spring metal formed into a shape to accept the lead therein, with the two pieces of the header contact 1184 spaced slightly to allow placement of the lead between the two pieces of the header contact 1184 such that they flex apart and allow the lead to pass into and reside within the area within the formed curves 1184A of each of the pieces of the header contact 1184. The shape of the header contact 1184, in some examples, is configured to flex against the lead and ensure good contact with the lead contact of the lead and, in turn, ensure a proper electrical connection. In some examples, the header contacts 1184 can be formed from one or more conductive metals, such as, but not limited to, platinum, platinum alloys, gold, MP35N, stainless steel, or the like. In some examples, the base 1186 can be formed from a ceramic material. In some examples, the header contacts 1184 coupled to the substrate 1186 can be used in conjunction with the sealing component 680 of FIG. 6, such that the header contacts 1184 are placed through the voids 684 with the formed curves 1184A being aligned with the groove 686 within the sealing component 680, thereby forming the bore within the header.

Figure 12:
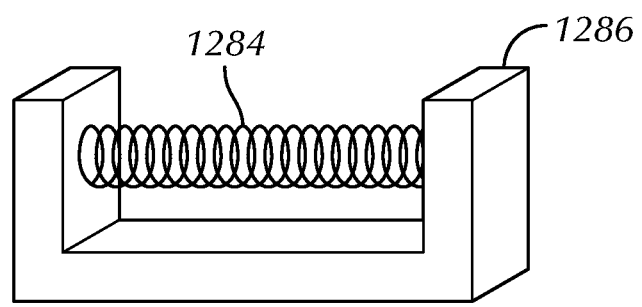
FIG. 12 is a perspective view of a header contact of an implantable medical device header in accordance with at least one example of the invention.

Referring to FIG. 12, in some examples, one or more header contacts 1284 can be formed from a spring to form one or more spring contacts. In some examples, the header contacts 1284 are attached to a base 1286. The one or more header contacts 1284, in some examples, are coupled to conductors within the header (such as, for instance, the headers 140, 440, 540 described above) that are routed down to the electronics within the housing (such as, for instance, the housings 102, 402, 502 described above).

In some examples, the one or more springs of the one or more header contacts 1284 are configured to reside within the bore (such as, for instance, the bores 180, 480, 580 described above) to accept a lead (such as, for instance, the lead 160 described above) and electrically couple to one or more lead contacts (such as, for instance, the lead contacts 162 described above). The spring of the header contact 1284, in some examples, is configured to flex against the lead and ensure good contact with the lead contact of the lead and, in turn, ensure a proper electrical connection. In some examples, the header contacts 1284 can be formed from one or more conductive metals, such as, but not limited to, platinum, platinum alloys, gold, MP35N, stainless steel, or the like. In some examples, the base 1286 can be formed from a ceramic material. In some examples, the header contacts 1284 coupled to the substrate 1286 can be used in conjunction with the sealing component 680 of FIG. 6, such that the header contacts 1284 are placed through the voids 684 with the springs being aligned with the groove 686 within the sealing component 680, thereby forming the bore within the header.

Figure 13:
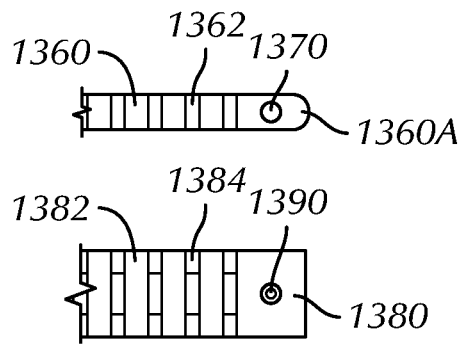
FIG. 13 is a top view of a proximal end of a lead of an implantable medical device and a bore of a header in accordance with at least one example of the invention, the bore including a positioning feature disposed within the bore and the lead including a corresponding lead feature proximate the proximal end of the lead.
Figure 14:
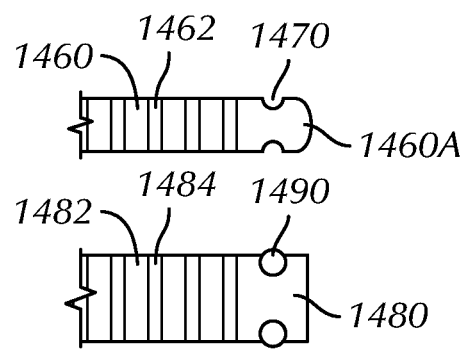
FIG. 14 is a top view of a proximal end of a lead of an implantable medical device and a bore of a header in accordance with at least one example of the invention, the bore including a positioning feature disposed within the bore and the lead including a corresponding lead feature proximate the proximal end of the lead.
Figure 15:
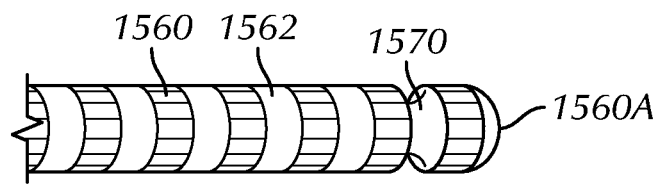
FIG. 15 is a top view of a proximal end of a lead of an implantable medical device in accordance with at least one example of the invention, the bore including a positioning feature disposed within the bore and the lead including a corresponding lead feature proximate the proximal end of the lead.

Referring to FIGS. 13-15, in some examples, a positioning feature 1390, 1490 is disposed within a bore 1380, 1480. In some examples, the positioning feature 1390, 1490 is configured to interact with a corresponding lead feature 1370, 1470, 1570 proximate a proximal end 1360A, 1460A, 1560A of a lead 1360, 1460, 1560. With the proximal end 1360A, 1460A, 1560A of the lead 1360, 1460, 1560 disposed within the bore 1380, 1480 and the positioning feature 1390, 1490 interacting with the lead feature 1370, 1470, 1570, in some examples, the at least one lead contact 1362, 1462, 1562 aligns with the at least one header contact 1384, 1482 to allow the at least one lead contact 1362, 1462, 1562 to electrically couple to the at least one header contact 1384, 1484. That is, in some examples, the lead feature 1370, 1470, 1570 and the positioning feature 1390, 1490 are located on the lead 1360, 1460, 1560 and within the bore 1380, 1480, respectively, to ensure that each of the one or more lead contacts 1362, 1462, 1562 are aligned with the one or more header contacts 1384, 1484 with the lead 1360, 1460, 1560 positioned within the bore 1380, 1480 and the positioning feature 1390, 1490 interacting with the lead feature 1370, 1470, 1570, such that proper electrical connection is made between the one or more header contacts 1384, 1484 and the corresponding one or more lead contacts 1362, 1462, 1562, thereby providing for proper operation of the one or more lead electrodes (such as, for example, the lead electrodes 164 described above) by the electronics of the implantable device (such as, for instance, the implantable devices 100, 400, 500 described above).

In some examples, referring specifically to FIG. 13, the positioning feature 1390 includes a pin 1390 disposed within the bore 1380 and the lead feature 1370 includes a corresponding hole 1370 within the lead 1360 proximate the proximal end 1360A of the lead 1360. In some examples, the hole 1370 is complementary to the pin 1390, such that, with the proximal end 1360A of the lead 1360 disposed within the bore 1380 and the pin 1390 disposed within the hole 1370 of the lead 1360, the lead 1360 is positioned within the bore 1380 to allow the at least one lead contact 1362 to align with and electrically couple to the at least one header contact 1384. Although the positioning feature 1390 of the bore 1380 is shown in FIG. 13 as a pin 1390 and the lead feature 1370 is shown as a corresponding hole 1370 in the present examples, it is contemplated, in other examples, that the positioning feature 1390 of the bore 1380 includes a hole and the lead feature 1370 includes a corresponding pin or that each of the positioning feature 1390 and the lead feature 1370 includes at least a pin and a hole or another combination of protrusions, bumps, notches, grooves, or the like, such that the positioning feature(s) and the lead feature(s) interact with each other to facilitate proper placement and/or alignment of the one or more leads 1360 within the one or more bores 1380.

Referring now specifically to FIG. 14, in some examples, the positioning feature 1490 includes a protrusion 1490 disposed within the bore 1480 and the lead feature 1470 includes a corresponding indentation 1470 within the lead 1460 proximate the proximal end 1460A of the lead 1460. In some examples, the protrusion 1490 includes one or more radially-extending bumps 1490 extending into and disposed at least partially around the bore 1480 and the indentation 1470 includes one or more notches 1470 disposed within and extending at least partially radially around the lead 1460. In the example shown in FIG. 14, the positioning feature 1490 includes two diametrically-opposed, radially-extending bumps 1490 extending into the bore 1480 and the lead feature 1470 includes two corresponding notches 1470 disposed within and extending at least partially radially around the lead 1460. In some examples, the bumps 1490 are made of a variety of materials strong enough to provide the positioning requirements for the lead 1460. In various examples, various configurations of numbers, sizes, and/or positioning of the notches 1470 and bumps 1490 can be used. Changing numbers, sizes, and/or positioning of the notches 1470 and bumps 1490 can provide indexing to align the lead 1460 in a certain direction and/or inhibit an incorrect lead from being used with the implantable device. Although the positioning feature 1490 of the bore 1480 is shown in FIG. 14 as bumps 1490 and the lead feature 1470 is shown as corresponding notches 1470 in the present examples, it is contemplated, in other examples, that the positioning feature 1490 of the bore 1480 includes a notch and the lead feature 1470 includes a corresponding bump or that each of the positioning feature 1490 and the lead feature 1470 includes at least a bump and a notch or another combination of protrusions, bumps, notches, grooves, or the like, such that the positioning feature(s) and the lead feature(s) interact with each other to facilitate proper placement and/or alignment of the one or more leads 1460 within the one or more bores 1480.

Referring specifically to FIG. 15, the positioning feature, in some examples, includes a protrusion disposed within the bore and the lead feature 1570 includes a corresponding indentation 1570 within the lead proximate the proximal end 1560A of the lead 1560. In some examples, the indentation 1570 is complementary to the protrusion, such that, with the proximal end of the lead disposed within the bore and the protrusion disposed within the indentation 1570 of the lead 1560, the lead 1560 is positioned within the bore to allow the at least one lead contact 1562 to align with and electrically couple to the at least one header contact. In some examples, the protrusion includes a bump extending into the bore and the indentation 1570 includes a notch 1570 within the lead 1560. In further examples, the protrusion includes a radially-extending bump extending into and disposed completely around the bore and the indentation 1570 includes a groove 1570 disposed within and extending completely radially around the lead 1560. In some examples, the protrusion is similar to the protrusion 590 of the bore 580 shown in FIG. 5. Such a configuration can allow rotation of the lead 1560 within the bore, if desired. Although the positioning feature of the bore is described as a bump and the lead feature 1570 is shown in FIG. 15 as a corresponding groove 1570 in the present examples, it is contemplated, in other examples, that the positioning feature of the bore includes a groove and the lead feature 1570 includes a corresponding bump or that each of the positioning feature and the lead feature 1570 includes at least a bump and a groove or another combination of protrusions, bumps, notches, grooves, or the like, such that the positioning feature(s) and the lead feature(s) interact with each other to facilitate proper placement and/or alignment of the one or more leads 1560 within the one or more bores.

In some examples, two or more different positioning features 1390, 1490 and corresponding lead features 1370, 1470, 1570 can be used in the same implantable device. In various examples, the positioning features 1390, 1490 can inhibit lead extraction when the header is secured in place. In this way, the lead positioning features 1390, 1490 allow an implantable device design that does not require set screws or other such fasteners to fix the lead within the header. Also, because contact alignment is controlled by design (not by insertion through a hole like typical headers), the contact pitch can be tightly controlled. In this way, the size of the header and, in turn, the implantable device, can be reduced from a typical header and implantable device.

In various examples, referring to FIGS. 1-15, one or more header contacts 184, 484, 584, 784, 884, 984, 1184, 1284 are placed in one or more rows in the header 140, 440, 540 separated by one or more seal members 182, 482, 582, 682, 1382, 1482 that provide electrical insulation and inhibit liquid ingress or electrical insulation. In some examples, the header contacts 184, 484, 584, 784, 884, 984, 1184, 1284 and seal members 182, 482, 582, 682, 1382, 1482 create a groove within the header 140, 440, 540 in which the lead 160, 860, 960, 1360, 1460, 1560 can be placed. After the one or more leads 160, 860, 960, 1360, 1460, 1560 are placed in the header 140, 440, 540, the first and second header portions 142, 144, 442, 444, 542, 544 are placed in the closed configuration to secure the one or more leads 160, 860, 960, 1360, 1460, 1560 within the header 140, 440, 540.

The present inventors have recognized various advantages of the subject matter described herein. The present inventors have recognized, among other things, that the present subject matter can be used to provide an implantable medical device that is smaller in size and higher in channel count than a conventional implantable medical device. In various examples, the present subject matter is advantageous in that it provides for very low insertion force to be applied to the lead during insertion of the lead into a header or other component of an implantable medical device, thereby inhibiting or lessening damage to the lead during an implant procedure and connection of the lead to the implantable medical device. In some examples, the present invention allows for connection and fixation of more than one multi-contact lead in a single operation. In some examples, the present invention can employ a positioning feature to facilitate alignment of the lead and the header contacts. In some examples, the present invention can employ a lead securing feature to inhibit the lead from moving without the need for a set screw, thereby eliminating the possibility of a set screw pressing on and potentially damaging the lead. While various advantages of the exemplary systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A header of an implantable device, the implantable device including a housing and a lead, the housing including electronics disposed within the housing, the lead including an elongate body with a proximal end and a distal end, the lead including at least one lead contact proximate the proximal end and at least one lead electrode proximate the distal end, the header comprising:
a first header portion;
a second header portion at least partially disengageable from the first header portion, wherein the header includes:
a closed configuration in which the first header portion is fully engaged with the second header portion; and
an open configuration in which the first header portion is at least partially disengaged from the second header portion;
at least one bore within the header sized and shaped to accommodate the proximal end of the lead, the bore including a bore opening in a wall of the header, the bore being split substantially longitudinally to form a first bore portion and a second bore portion, the first bore portion forming a first channel disposed within the first header portion and including a first channel opening in a first surface of the first header portion along a length of the first channel, and the second bore portion forming a second channel disposed within the second header portion and including a second channel opening in a second surface of the second header portion along a length of the second channel;
at least one header contact disposed within the bore and configured to electrically couple to the lead contact with the proximal end of the lead disposed within the bore; and
a positioning feature disposed within the bore, the positioning feature configured to interact with a corresponding lead feature proximate the proximal end of the lead, wherein, with the proximal end of the lead disposed within the bore and the positioning feature interacting with the lead feature, the at least one lead contact aligns with the at least one header contact to allow the at least one lead contact to electrically couple to the at least one header contact, wherein:
with the header in the open configuration, the length of the first channel is accessible to allow the lead to be inserted laterally into the first channel through the first channel opening; and
with the header in the closed configuration, the first surface of the first header portion abuts the second surface of the second header portion so that the first bore portion and the second bore portion form the bore accessible only through the bore opening in the wall of the header, such that, with the proximal end of the lead disposed within the bore, the elongate body of the lead extends distally from the bore opening.

2. The header of claim 1, wherein the positioning feature includes a pin disposed within the bore and the lead feature includes a corresponding hole within the lead proximate the proximal end of the lead, the hole being complementary to the pin, such that, with the proximal end of the lead disposed within the bore and the pin disposed within the hole of the lead, the lead is positioned within the bore to allow the at least one lead contact to align with and electrically couple to the at least one header contact.

3. The header of claim 1, wherein the positioning feature includes a protrusion disposed within the bore and the lead feature includes a corresponding indentation within the lead proximate the proximal end of the lead, the indentation being complementary to the protrusion, such that, with the proximal end of the lead disposed within the bore and the protrusion disposed within the indentation of the lead, the lead is positioned within the bore to allow the at least one lead contact to align with and electrically couple to the at least one header contact.

4. The header of claim 3, wherein the protrusion includes a bump extending into the bore and the indentation includes a notch within the lead.

5. The header of claim 3, wherein the protrusion includes one or more radially-extending bumps extending into and disposed at least partially around the bore and the indentation includes a groove disposed within and extending at least partially radially around the lead.

6. The header of claim 1, wherein the at least one header contact includes a spring.

7. The header of claim 1, wherein the at least one header contact includes a spring contact.

8. The header of claim 1, comprising a seal member including a first seal portion disposed within the first bore portion of the first header portion and a second seal portion disposed within the second bore portion of the second header portion, wherein, with the header in the closed configuration and the proximal end of the lead within the bore, the first seal portion abuts the second seal portion, and the first seal portion and the second seal portion extend into the bore to abut the elongate body of the lead.

9. The header of claim 1, wherein the first header portion is pivotably coupled to the second header portion, such that the second header portion is rotatable with respect to the first header portion from being fully engaged with the first header portion in the closed configuration to being partially disengaged from the first header portion in the open configuration.

10. The header of claim 9, wherein the first header portion is pivotably coupled to the second header portion at a hinge.

11. The header of claim 1, wherein the first header portion is removably coupled to the second header portion, such that the second header portion is fully engaged with the first header portion in the closed configuration and fully disengaged and removed from the first header portion in the open configuration.

12. The header of claim 11, wherein the first header portion is removably coupled to the second header portion using securement members.

13. An implantable device comprising:
a housing including electronics disposed within the housing;
a lead including an elongate body with a proximal end and a distal end, the lead including at least one lead contact proximate the proximal end and at least one lead electrode proximate the distal end; and
a header attached to the housing, the header configured to engage with the lead and electrically couple the lead to the electronics disposed within the housing, the header including:
a first header portion;
a second header portion at least partially disengageable from the first header portion, wherein the header includes:
a closed configuration in which the first header portion is fully engaged with the second header portion; and
an open configuration in which the first header portion is at least partially disengaged from the second header portion;
at least one bore within the header sized and shaped to accommodate the proximal end of the lead, the bore including a bore opening in a wall of the header, the bore being split substantially longitudinally to form a first bore portion and a second bore portion, the first bore portion forming a first channel disposed within the first header portion and including a first channel opening in a first surface of the first header portion along a length of the first channel, and the second bore portion forming a second channel disposed within the second header portion and including a second channel opening in a second surface of the second header portion along a length of the second channel;
at least one header contact disposed within the bore and configured to electrically couple to the lead contact with the proximal end of the lead disposed within the bore; and
a positioning feature disposed within the bore, the positioning feature configured to interact with a corresponding lead feature proximate the proximal end of the lead, wherein, with the proximal end of the lead disposed within the bore and the positioning feature interacting with the lead feature, the at least one lead contact aligns with the at least one header contact to allow the at least one lead contact to electrically couple to the at least one header contact, wherein:
with the header in the open configuration, the length of the first channel is accessible to allow the lead to be inserted laterally into the first channel through the first channel opening; and
with the header in the closed configuration, the first surface of the first header portion abuts the second surface of the second header portion so that the first bore portion and the second bore portion form the bore accessible only through the bore opening in the wall of the header, such that, with the proximal end of the lead disposed within the bore, the elongate body of the lead extends distally from the bore opening.

14. The implantable device of claim 13, wherein the positioning feature includes a pin disposed within the bore and the lead feature includes a corresponding hole within the lead proximate the proximal end of the lead, the hole being complementary to the pin, such that, with the proximal end of the lead disposed within the bore and the pin disposed within the hole of the lead, the lead is positioned within the bore to allow the at least one lead contact to align with and electrically couple to the at least one header contact.

15. The implantable device of claim 13, wherein the positioning feature includes a protrusion disposed within the bore and the lead feature includes a corresponding indentation within the lead proximate the proximal end of the lead, the indentation being complementary to the protrusion, such that, with the proximal end of the lead disposed within the bore and the protrusion disposed within the indentation of the lead, the lead is positioned within the bore to allow the at least one lead contact to align with and electrically couple to the at least one header contact.

16. The implantable device of claim 15, wherein the protrusion includes a bump extending into the bore and the indentation includes a notch within the lead.

17. The implantable device of claim 13, wherein the header includes a seal member including a first seal portion disposed within the first bore portion of the first header portion and a second seal portion disposed within the second bore portion of the second header portion, wherein, with the header in the closed configuration and the proximal end of the lead within the bore, the first seal portion abuts the second seal portion, and the first seal portion and the second seal portion extend into the bore to abut the elongate body of the lead.

18. The implantable device of claim 13, wherein the first header portion is pivotably coupled to the second header portion, such that the second header portion is rotatable with respect to the first header portion from being fully engaged with the first header portion in the closed configuration to being partially disengaged from the first header portion in the open configuration.

19. The implantable device of claim 13, wherein the first header portion is removably coupled to the second header portion, such that the second header portion is fully engaged with the first header portion in the closed configuration and fully disengaged and removed from the first header portion in the open configuration.

20. A header of an implantable device, the header comprising:
- a first header portion;
- a second header portion at least partially disengageable from the first header portion, wherein the header includes:
  - a closed configuration in which the first header portion is fully engaged with the second header portion; and
  - an open configuration in which the first header portion is at least partially disengaged from the second header portion;
- at least one bore within the header sized and shaped to accommodate a proximal end of a lead, the bore including a bore opening in a wall of the header, the bore being split substantially longitudinally to form a first bore portion and a second bore portion, the first bore portion forming a first channel disposed within the first header portion and including a first channel opening in a first surface of the first header portion along a length of the first channel, and the second bore portion forming a second channel disposed within the second header portion and including a second channel opening in a second surface of the second header portion along a length of the second channel;
- at least one header contact disposed within the bore and configured to electrically couple to a lead contact with the proximal end of the lead disposed within the bore; and
- a positioning feature disposed within the bore, the positioning feature configured to interact with a corresponding lead feature proximate the proximal end of the lead, wherein:
  - with the header in the open configuration, the length of the first channel and the length of the second channel are accessible to allow a lead to be inserted laterally into either the first channel through the first channel opening or the second channel through the second channel opening; and
  - with the header in the closed configuration, the first surface of the first header portion abuts the second surface of the second header portion so that the first bore portion and the second bore portion form the bore accessible only through the bore opening in the wall of the header.

* * * * *